United States Patent [19]

Berg

[11] Patent Number: 5,762,765
[45] Date of Patent: Jun. 9, 1998

[54] SEPARATION OF ETHANOL, ISOPROPANOL AND WATER MIXTURES BY AZEOTROPIC DISTILLATION

[76] Inventor: Lloyd Berg, 1314 S. 3rd Ave., Bozeman, Mont. 59715

[21] Appl. No.: 837,101

[22] Filed: Apr. 14, 1997

[51] Int. Cl.$^6$ .............................. B01D 3/36; C07C 29/84
[52] U.S. Cl. .................... 203/60; 203/19; 568/913; 568/916
[58] Field of Search ................... 203/68, 69, 60, 203/19, 57, 18; 568/913, 916

[56] References Cited

U.S. PATENT DOCUMENTS

| | | | |
|---|---|---|---|
| 2,050,513 | 8/1936 | Bussum et al. | 203/18 |
| 3,898,291 | 8/1975 | Darsi et al. | 203/99 |
| 3,960,672 | 6/1976 | Ester et al. | 203/18 |
| 4,161,429 | 7/1979 | Baiel et al. | 568/913 |
| 4,382,843 | 5/1983 | Black | 203/69 |
| 4,636,284 | 1/1987 | English et al. | 203/19 |
| 5,084,142 | 1/1992 | Berg et al. | 203/60 |
| 5,085,739 | 2/1992 | Berg et al. | 568/916 |
| 5,338,411 | 8/1994 | Berg | 203/63 |
| 5,449,440 | 9/1995 | Rescalli et al. | 203/18 |

FOREIGN PATENT DOCUMENTS 0762974  12/1956  United Kingdom ............... 203/18

*Primary Examiner*—Virginia Manoharan

[57] ABSTRACT

Ethanol, isopropanol and water cannot be separated from each other by rectification because of the presence of minimum azeotropes. They are readily separated by azeotropic distillation. Effective agents are cyclopentane for ethanol from water, methyl acetate for isopropanol from water.

1 Claim, No Drawings

SEPARATION OF ETHANOL, ISOPROPANOL AND WATER MIXTURES BY AZEOTROPIC DISTILLATION

FIELD OF THE INVENTION

This invention relates to a method for separating ethanol, isopropanol and water mixtures using certain organic compounds as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Ethanol and isopropanol form minimum boiling azeotropes with water and a mixture of these three form a minimum boiling ternary azeotrope and cannot be separated from each other by conventional distillation or rectification. Azeotropic distillation would be an attractive method of effecting the separation of these three if agents can be found that (1) will create a large apparent relative volatility among these three and (2) are easy to recover. Table 2 shows the relative volatility required to obtain 99% purity. With an agent giving a relative volatility of 2.5, only 14 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.5 | 22 | 30 |
| 2.0 | 12 | 16 |
| 2.5 | 10 | 14 |

OBJECTIVE OF THE INVENTION

The object of this invention is to provide a process or method of azeotropic distillation that will enhance the relative volatility of ethanol, isopropanol and water in their separation in a rectification column. It is a further object of this invention to identify organic compounds which in addition to the above constraints, are stable, can be separated from ethanol, isopropanol and water and recycled to the column with little decomposition.

SUMMARY OF THE INVENTION

The objects of this invention are provided by a process for separating ethanol, isopropanol and water which entails the use of certain organic compounds as the agent in azeotropic distillation.

TABLE 3

Effective Azeotropic Distillation Agents For Separating Ethanol From Ethanol - Isopropanol - Water Mixtures

| Compound | Relative Volatility |
|---|---|
| Cyclopentane | 2.7 |

TABLE 4

Effective Azeotropic Distillation Agents For Separating Isopropanol From Ethanol - Isopropanol - Water Mixtures

| Compounds | Relative Volatility |
|---|---|
| Methyl acetate | 1.5 |
| Methyl formate | 1.5 |

DETAILED DESCRIPTION OF THE INVENTION

I have discovered that certain organic compounds will greatly improve the relative volatility between ethanol, isopropanol and water and permit the separation by rectification when employed as the agent in azeotropic distillation. Table 3 lists the compound, cyclopentane, which is effective in separating ethanol from isopropanol and water by azeotropic distillation. Table 4 shows the compounds, cyclopentane, methyl acetate and methyl formate, that are effective in separating isopropanol from ethanol and water.

THE USEFULNESS OF THE INVENTION

The usefulness of this invention can be demonstrated by referring to the data presented in Tables 1, 2 and 3. All of the agents show that ethanol, isopropanol and water can be separated from each other by means of azeotropic distillation in a rectification column and that the ease of separation as measured by relative volatility is considerable.

WORKING EXAMPLES

Example 1

Fifty grams of ethanol, isopropanol and water mixture and 50 grams of cyclopentane were charged to a vapor-liquid equilibrium still and refluxed for five hours. The vapor composition was 16.7% water, 76.2% ethanol and 7.1% isopropanol; the liquid composition was 35.1% water, 58.8% ethanol and 6.1% isopropanol. This is a relative volatility of ethanol to water of 2.7.

Example 2

Fifty grams of ethanol, isopropanol and water mixture and 50 grams of methyl acetate were charged to a vapor-liquid equilibrium still and refluxed for six hours. The vapor composition was 22.9% water, 58.3% ethanol and 18.8% isopropanol; the liquid composition was 28.6% water, 56.2% ethanol and 15.2% isopropanol. This is a relative volatility of isopropanol to water of 1.5.

I claim:

1. A method of recovering isopropanol from a mixture of isopropanol, ethanol and water which comprises distilling a mixture consisting of isopropanol, ethanol and water in the presence of an azeotrope forming agent, recovering the isopropanol and the azeotrope forming agent as overhead product and obtaining the ethanol and water as bottoms product, wherein said azeotrope forming agent consists of methyl acetate.

* * * * *